United States Patent
Zhang et al.

(10) Patent No.: US 11,219,419 B2
(45) Date of Patent: Jan. 11, 2022

(54) CT SCANNING DEVICE AND GANTRY THEREOF

(71) Applicant: General Electric Company, Schenectady, NY (US)

(72) Inventors: Xiaoyan Zhang, Beijing (CN); Chad A Smith, Waukesha, WI (US); Yan Guo Yang, Beijing (CN); Kiyomi Abeshima, Hino (JP)

(73) Assignee: General Electric Company, Schenectady, NY (US)

( * ) Notice: Subject to any disclaimer, the term of this patent is extended or adjusted under 35 U.S.C. 154(b) by 7 days.

(21) Appl. No.: 16/719,210

(22) Filed: Dec. 18, 2019

(65) Prior Publication Data
US 2020/0205752 A1 Jul. 2, 2020

(30) Foreign Application Priority Data
Dec. 27, 2018 (CN) .......................... 201811610519.6

(51) Int. Cl.
*A61B 6/03* (2006.01)
(52) U.S. Cl.
CPC .................................. *A61B 6/035* (2013.01)
(58) Field of Classification Search
CPC ..................................................... A61B 6/035
See application file for complete search history.

(56) References Cited

U.S. PATENT DOCUMENTS

| | | | | |
|---|---|---|---|---|
| 2,956,281 A | * | 10/1960 | McMillan | H01Q 1/424 343/872 |
| 4,939,763 A | * | 7/1990 | Pinneo | G03F 1/22 378/161 |
| 5,258,091 A | * | 11/1993 | Imai | G01T 7/00 216/12 |
| 5,329,569 A | * | 7/1994 | Spielman | G21K 1/10 378/140 |
| 6,103,401 A | * | 8/2000 | Okada | G02B 1/02 228/124.6 |
| 7,403,596 B1 | * | 7/2008 | Chaves | H05G 1/04 378/140 |
| 7,414,246 B2 | * | 8/2008 | Griesmer | G01T 1/2985 250/363.03 |
| 7,709,820 B2 | * | 5/2010 | Decker | G21K 1/00 250/505.1 |
| 7,737,424 B2 | * | 6/2010 | Xu | H01J 47/004 250/505.1 |

(Continued)

*Primary Examiner* — David P Porta
*Assistant Examiner* — Djura Malevic

(57) ABSTRACT

The present invention relates to a gantry of a CT scanning device comprising: a first housing having a first bore; a second housing having a second bore, disposed opposite to the first housing, wherein there is a gap between the first bore and the second bore, as a ray scanning bore; a scan window assembly comprising an annular window body having an inner surface and an outer surface, the scan window assembly being engaging-locked with the first housing and the second housing and sealing and covering the ray scanning bore. In this way, the engaging-lock can restrict deformation of the annular window body when an external force is applied on the scan window assembly, and the sealing can prevent liquid in the first and second housing from leaking out and prevent liquid inside the scan window assembly from leaking into the first and second housing.

11 Claims, 16 Drawing Sheets

(56) References Cited

U.S. PATENT DOCUMENTS

| | | | | |
|---|---|---|---|---|
| 8,431,904 B2* | 4/2013 | Lewellen | | A61B 6/037 |
| | | | | 250/363.03 |
| 8,494,119 B2* | 7/2013 | Andersson | | H01J 5/18 |
| | | | | 378/161 |
| 8,929,515 B2* | 1/2015 | Liddiard | | H01J 35/18 |
| | | | | 378/140 |
| 8,989,354 B2* | 3/2015 | Davis | | H01J 5/18 |
| | | | | 378/161 |
| 9,044,152 B2* | 6/2015 | Abenaim | | G01N 23/046 |
| 9,076,628 B2* | 7/2015 | Davis | | G21K 1/00 |
| 9,254,108 B2* | 2/2016 | Maki | | A61B 6/10 |
| 9,299,469 B2* | 3/2016 | Larson | | H01J 5/18 |
| 10,478,133 B2* | 11/2019 | Levy | | A61B 6/06 |
| 2008/0317209 A1* | 12/2008 | Sipila | | H01J 5/18 |
| | | | | 378/140 |
| 2010/0074411 A1* | 3/2010 | Chaves | | H01J 35/18 |
| | | | | 378/141 |
| 2012/0025110 A1* | 2/2012 | Davis | | H01J 5/18 |
| | | | | 250/505.1 |
| 2012/0134472 A1* | 5/2012 | Kaneko | | B32B 33/00 |
| | | | | 378/70 |
| 2012/0230465 A1* | 9/2012 | Matsuzawa | | A61B 6/035 |
| | | | | 378/13 |
| 2013/0053676 A1* | 2/2013 | Kemper | | A61B 6/035 |
| | | | | 600/407 |
| 2013/0077761 A1* | 3/2013 | Sipila | | G21K 1/02 |
| | | | | 378/161 |
| 2013/0094629 A1* | 4/2013 | Liddiard | | H01J 5/18 |
| | | | | 378/140 |
| 2014/0044240 A1* | 2/2014 | Pahlke | | H01J 5/18 |
| | | | | 378/161 |
| 2014/0064440 A1* | 3/2014 | Hara | | A61B 6/508 |
| | | | | 378/4 |
| 2014/0126689 A1* | 5/2014 | Hara | | A61B 6/0407 |
| | | | | 378/19 |
| 2015/0053640 A1* | 2/2015 | Kostamo | | B32B 38/0004 |
| | | | | 216/24 |
| 2015/0265229 A1* | 9/2015 | Maki | | A61B 6/032 |
| | | | | 378/4 |
| 2016/0374632 A1* | 12/2016 | David | | A61B 6/4423 |
| | | | | 378/161 |
| 2017/0112454 A1* | 4/2017 | Yun | | A61B 6/0407 |
| 2018/0209877 A1* | 7/2018 | Hendrickx | | G01N 1/38 |
| 2019/0143145 A1* | 5/2019 | Laurence, Jr. | | A61B 34/10 |
| | | | | 600/1 |
| 2020/0121267 A1* | 4/2020 | Deutschmann | | A61B 6/105 |
| 2020/0137861 A1* | 4/2020 | Imaizumi | | A61B 6/4411 |
| 2020/0205752 A1* | 7/2020 | Zhang | | A61B 6/035 |

\* cited by examiner

CT SCANNING DEVICE AND GANTRY THEREOF

TECHNICAL FIELD

Embodiments of the present disclosure generally relate to a computer tomography (CT) imaging device, and more particularly to a CT scanning device and a gantry thereof.

BACKGROUND

A gantry is a very important part in a CT imaging device, which can hold X-ray tubes and detectors. The gantry has an annular scan window through which X-rays used for imaging emit in and out. In operation, an X-ray source (e.g., X-ray tube) and a detector rotate around an object to be imaged, or the object to be imaged rotates while the X-ray source and the detector remain stationary.

International Standard for Medical Electrical Equipment, IEC60601 requires that external parts of an enclosure are to be subject to a steady test force of 250 N when evaluating for safety of a device, which is to simulate the type of force a patient or operator could apply to the gantry. For CT scanning device, the scan window should be as thin as possible to attenuate the least amount of X-rays, thereby allowing the system to image larger patients. However, as the scan window gets thinner, deformation from the required 250N test force could result in the scan window coming in contact with the rotating parts of the CT scanning device, thus creating a potential hazard for the patient or operator who is in the cavity of the scanning device.

Accordingly, there is a need for a new approach for locking the scan window, which can satisfy: 1) meeting the 250N push requirement without contacting the rotating parts; 2) being able to use a thinner material for the scan window; 3) the liquid seal between the housing of the scanning device and the scan window.

SUMMARY

The object of exemplary embodiments of the present invention is just to provide such a gantry of a CT scanning device, which can implement a low deformation scan window engaging-lock structure by means of hard or semi-hard engaging and have safety protection.

Specifically, an exemplary embodiment of the present invention provides a gantry of a CT scanning device comprising: a first housing having a first bore; a second housing having a second bore, disposed opposite to the first housing, wherein there is a gap, as a ray scanning bore, between the first bore and the second bore; a scan window assembly comprising an annular window body having an inner surface and an outer surface, the scan window assembly being engaging-locked with the first housing and the second housing and sealing and covering the ray scanning bore. In this way, the engaging-lock can restrict deformation of the annular window body when an external force is applied on the scan window assembly, and the sealing can prevent liquid in the first and second housing from leaking out and prevent liquid inside the scan window assembly from leaking into the first and second housing.

Preferably, the scan window assembly further comprises a first window engagement and a second window engagement disposed at both sides of the outer surface of the annular window body respectively, the first window engagement engaging with the first housing, and the second window engagement engaging with the second housing.

Preferably, the engaging of the first window engagement with the first housing and the engaging of the second window engagement with the second housing are implemented respectively by one of convex/concave surface engaging-lock, engaging-lock of rotational contact of convex/concave surface, engaging-lock of surfaces attached closely, adhesive engaging-lock and Velcro engaging-lock.

Preferably, in case of implementing by the convex/concave surface engaging-lock, the first and/or second window engagement comprises a tooth arrangement, the tooth arrangement having one or more layers of convex teeth in an axial direction of the annular window body, the first and/or second housing comprising one or more layers of concave tooth slots in the axial direction of the annular window body. More preferably, the shape and size of the convex teeth match those of the tooth slots.

Preferably, in case of implementing by the engaging-lock of rotational contact of convex/concave surface, the first window engagement comprises one or more flat teeth distributed along a circumferential direction of the annular window body, the second window engagement comprises one or more convex blocks distributed along the circumferential direction of the annular window body, the first housing comprising flat tooth slots for engaging with the one or more flat teeth, the second housing comprising one or more inclined or helical tooth slots for engaging with the one or more convex blocks.

Preferably, in case of implementing by the engaging-lock of surface attached closely, the first and/or second window engagement has a cylinder shape or cone shape and consists of semi-hard material, the first and/or second housing has a cylinder or cone hard internal surface corresponding thereto. More preferably, the semi-hard material is a semi-hard rubber material.

Preferably, in case of implementing by Velcro engaging-lock, the first and/or second window engagement and the corresponding first and/or second housing engagement are Velcro Hook and Velcro Loop, respectively, to form a set of Velcro engaging-locks.

Preferably, in case of implementing by adhesive engaging-lock, the engaging-lock of the first and/or second window engagement and the corresponding first and/or second housing engagement is formed by using an adhesive that can be disassembled multiple times.

Preferably, the first and/or second window engagement is continuous along a circumferential direction of the annular window body.

Preferably, the first and/or second window engagement has a plurality of sub-engagements along a circumferential direction of the annular window body.

Preferably, the first and/or second window engagement surrounds an entire circumference of the annular window body, or the first and/or second window engagement surrounds a partial circumference of the annular window body.

Preferably, the scan window assembly further comprises an elastic band disposed at both sides of the inner surface of the annular window body along edges of the annular window body, to provide pressure to press the scan window assembly towards the first and second housing along its radially outward direction over an entire circumference.

Preferably, the scan window assembly further comprises an elastic soft sealing material disposed at both sides of the outer surface of the annular window body along edges of the annular window body, the elastic soft sealing material being compressible and deformable under an elastic pressure of the scan window assembly to achieve the sealing of the first housing and the scan window assembly, and the sealing of the second housing and the scan window assembly. In this way, liquid in the first and second housing can be prevented from leaking out and liquid inside the scan window assembly can be prevented from leaking into the first and second housing.

Preferably, the first housing further includes a first housing engagement disposed on an inner side of the first bore adjacent to the ray scanning bore, for being engaging-locked with the scanning window assembly; the second housing further includes a second housing engagement disposed on an inner side of the second cavity adjacent to the ray scanning bore, for being engaging-locked with the scanning window assembly. As an example, the first and/or second housing engagement is continuous along a circumferential direction of the annular window body. As another example, the first and/or second housing engagement has a plurality of sub-engagements along a circumferential direction of the annular window body.

Preferably, the first housing further includes a first sealing region located in the first bore, for forming a seal with a corresponding first elastic soft sealing material of the scanning window assembly; the second housing further includes a second sealing region located in the second bore, for forming a seal with a corresponding second elastic soft sealing material of the scanning window assembly.

Preferably, the first and/or second housing engagement surrounds an entire circumference of the annular window body, or the first and/or second housing engagement surrounds a partial circumference of the annular window body.

Preferably, the annular window body is made of a thin layer of material with low X-ray attenuation. More preferably, the thin layer of material with low X-ray attenuation comprises polycarbonate.

Preferably, the annular window body itself can have a function of tooth arrangement to directly and tightly engaging-lock with the first housing and the second housing.

According to another exemplary embodiment of the present invention, a CT scanning device is provided, which comprises: a gantry as described above; and an X-ray source and detector assembly provided on the gantry.

In the gantry and the CT scanning device according to the above exemplary embodiments, the scan window assembly, when placed inside the first bore of the first housing and the second bore of the second housing and engaging-locked with the first housing and the second housing and seal, has a resilience force for restoring the original shape, which presses the scan window assembly toward the first housing and the second housing to achieve tight engaging-lock and seal.

In addition, the scan window assembly has certain deformability to facilitate the installation and removal of the scan window, and when there is no external force or the scan window assembly is removed from the scanning device, all components on the scanning device and the scan window assembly can return to its original shape under the resilience force.

Moreover, the scan window assembly has safety protection, and has certain deformability and resilience to return to its original shape when there is no external force, and the first window engagement, the second window engagement, the elastic soft sealing material and the elastic band are all fixed on the annular window body.

Further, when a force from a patient or an operator may be applied to the scan window assembly, the stressed area of the scan window assembly tends to move toward the radial direction, and the vicinity of the stressed area tends to tilt, but the hard or semi-hard engaging-lock between the scan window assembly and the first and second housing, i.e., the engaging-lock with sufficient rigidity will block the movement and tilting of the annular window body, thereby significantly reducing the deformation of the annular window body. The hard engaging-lock described herein means that there is little or no deformation between the engagement lockers under the effect of pressure. The semi-hard engaging-lock described herein means that there is some but not much deformation between the engagement lockers under the effect of pressure. The elastic soft sealing described herein means that the elastic soft sealing material has a large deformation under the effect of pressure.

BRIEF DESCRIPTION OF THE DRAWINGS

The invention may be better understood by the description of the exemplary embodiments of the present invention in conjunction with the accompanying drawings, in which.

DETAILED DESCRIPTION

In the following, specific embodiments of the present invention will be described. It should be noted that, in the detailed description of these embodiments, all features of the actual embodiments may not be described in detail for conciseness of the description. It should be understood, in actual implementation of any one of the embodiments, just as in any one engineering project or designing project, in order to achieve the developers' specific goals and in order to meet system-related or business-related restrictions, a variety of concrete decisions are often made, and this varies from one implementation to another. In addition, it should also be understood, although the effort made in such developing process may be complex and time-consuming, some variations such as design, manufacture and production on the basis of the technical contents disclosed in the disclosure are just customary technical means in the art for one of ordinary skilled in the art associated with the contents disclosed in the present disclosure, which should not be regarded as insufficient disclosure of the present disclosure.

Unless otherwise defined, all technical or scientific terms used in the claims and the description should be interpreted in the ordinary sense to one of ordinary skills in the art to which this invention belongs. The terms "first", "second," and similar terms used in the description and claims of the present invention do not imply any order, quantity, or importance, but are merely used to distinguish between different components. "One", "a/an", or similar terms do not imply any limitation on the number, but rather means "at least one". "Including" or "comprising" and the like means that an element or item appearing before "including" or "comprising" an element or item and its equivalents listed after "including" or "comprising", and does not exclude other elements or items. "Connected", "coupled" and the like are not limited to physical or mechanical connections, nor are they limited to direct or indirect connections.

Figure 1:
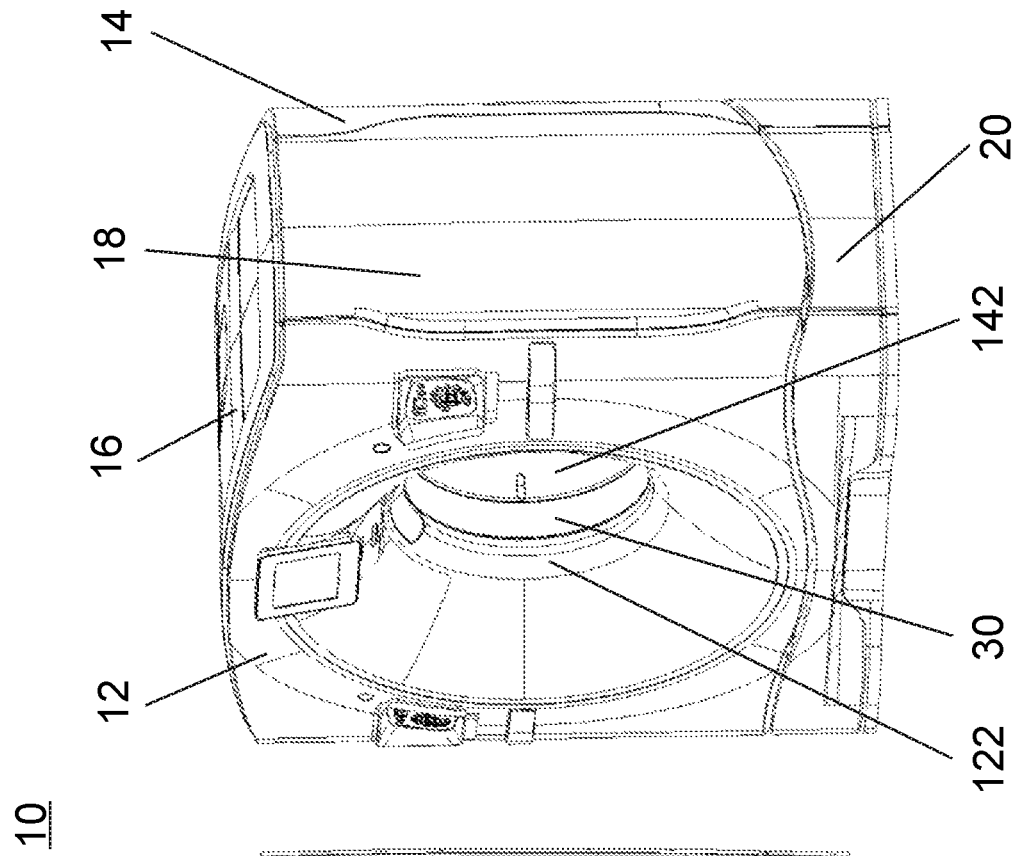
FIG. 1 illustrates a schematic diagram of a gantry 10 of a CT scanning device according to an exemplary embodiment of the present invention.
Figure 1:
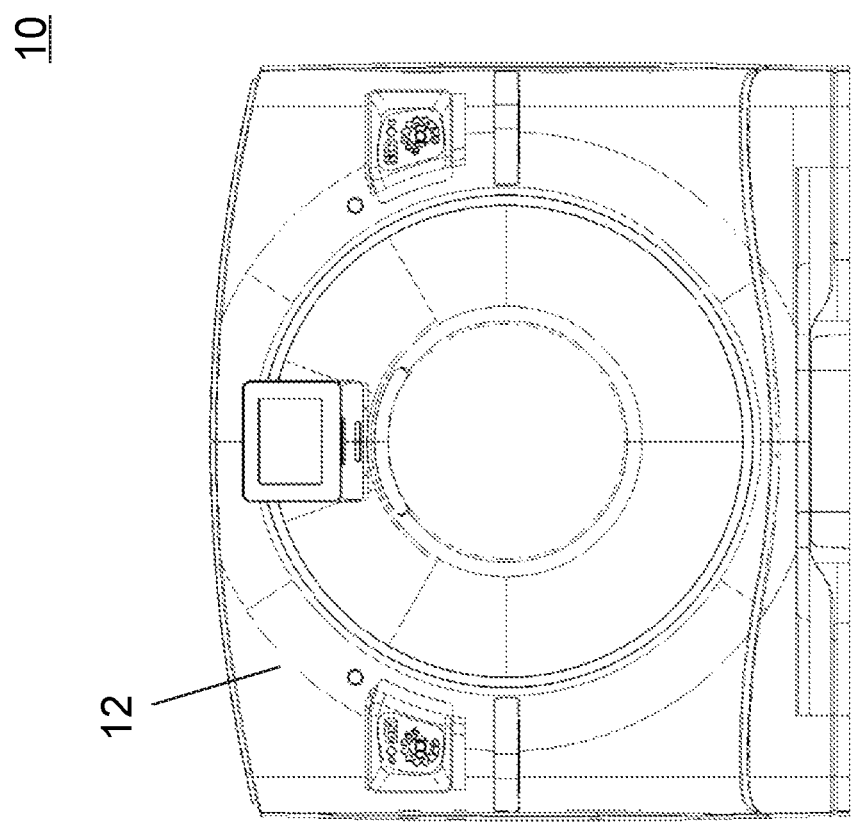

FIG. 1 illustrates a schematic diagram of a gantry 10 of a CT scanning device according to an embodiment of the present invention. Referring to FIG. 1, a CT scanning device includes a gantry 10 comprising a first housing 12, a second housing 14, a top cover 16, side covers 18, a base cover 20, and a scan window assembly 30. An X-ray source and a detector assembly (not shown) may be oppositely provided on the gantry 10. In operation, the X-ray source projects a beam of X-rays toward a detector (e.g., detector array) on the opposite side of the gantry 10 of the scanning device through the scan window assembly 30 and a patient (not shown), and the detector assembly collects the data of the attenuated beam of X-rays. The first housing 12, the second housing 14, the top cover 16, the side covers 18 and the base cover 20 of the gantry 10 may be mounted and dismounted independently, or may also be formed partly-integrated or entirely-integrated. For example, the first housing 12 and the side covers 18 may be a single member formed integrally, alternatively, the second housing 14, the side covers 18 and the base cover 20 may be a single member formed integrally, among other examples. Particularly, in some embodiments, the enclosure of the gantry 10 may only be composed of the first housing 12 and the second housing 14.

Figure 2:
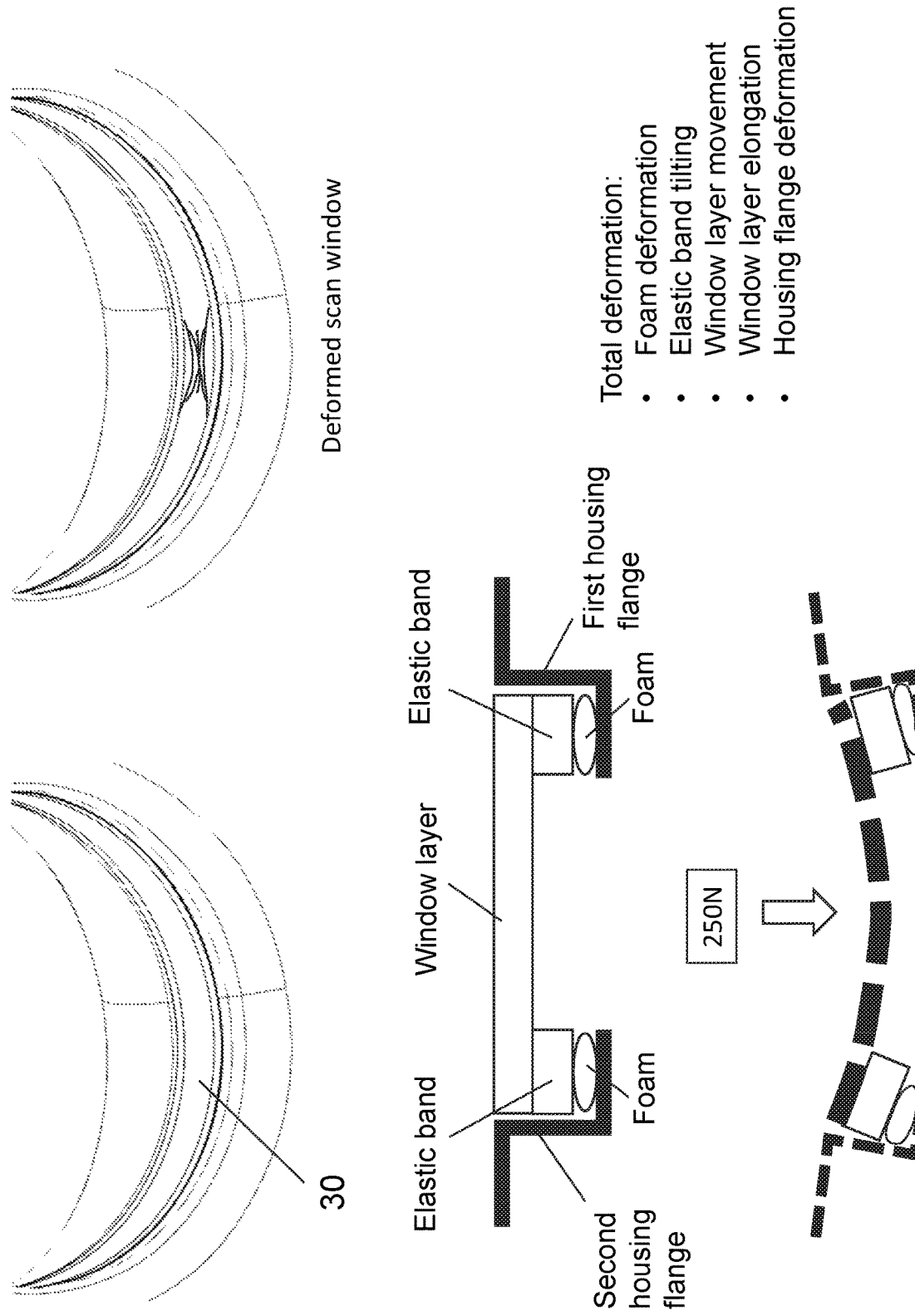
FIG. 2 illustrates schematic diagram of deformation of a scan window in a conventional CT scanning device.

The first housing 12 and the second housing 14 may comprise a first bore 122 and a second bore 142 therethrough respectively. There is a gap between the first bore 122 of the first housing 12 and the second bore 142 of the second housing 14, i.e., a ray scanning bore. X-rays can pass through the gap and the patient for CT scanning. The scan window assembly 30 covers the gap, thereby preventing the liquid inside the scanning device from leaking out of the gantry 10 of the scanning device or the external liquid penetrating into the gantry 10 of the scanning device; meanwhile, when a force is applied on the scan window assembly 30 by a patient or an operator, they do not contact the rotating parts to ensure safety, and in this way, the entire structure can have a reduced X-ray attenuation and is easy to assembly and disassembly As shown in FIG. 2, in a conventional CT scanning device, when a force is applied on a window layer of a scan window assembly, a larger deformation would occur to the window layer of the scan window assembly. Such deformation may be attributed to 5 factors: foam deformation, elastic band tilting, window layer movement, window layer elongation, deformations of the first bore's side of the first housing adjacent to the ray scanning bore and the second bore's side of the second housing adjacent to the ray scanning bore. The first three factors of which are dominated. When subjected to 250N test, the deformation of the scan window of the conventional CT scanning device is relatively large.

First Embodiment

Figure 3:
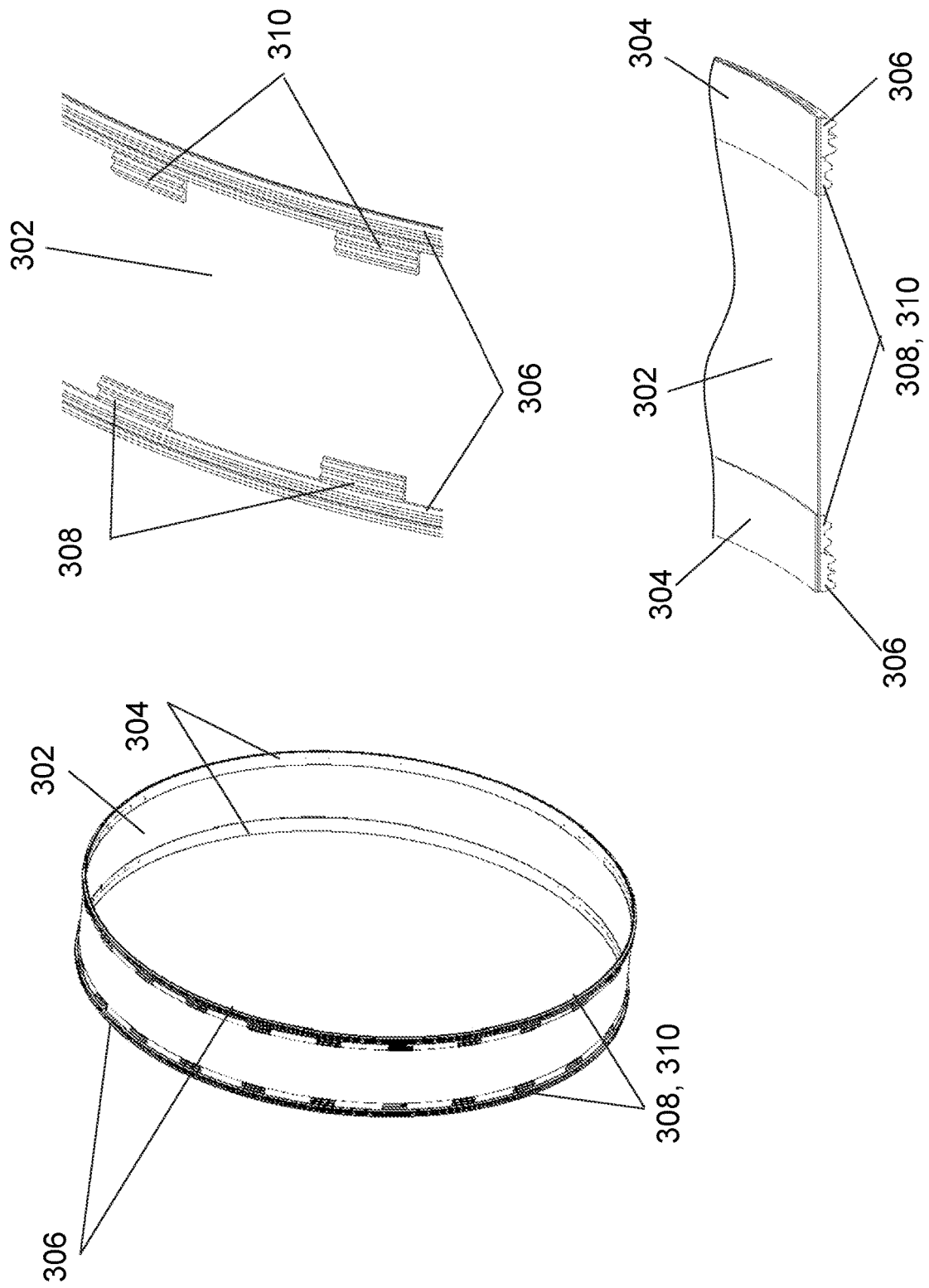
FIG. 3 illustrates a schematic diagram of a scan window assembly 30 for a gantry 10 for a CT scanning device according to a first embodiment of the present invention.
Figure 4:
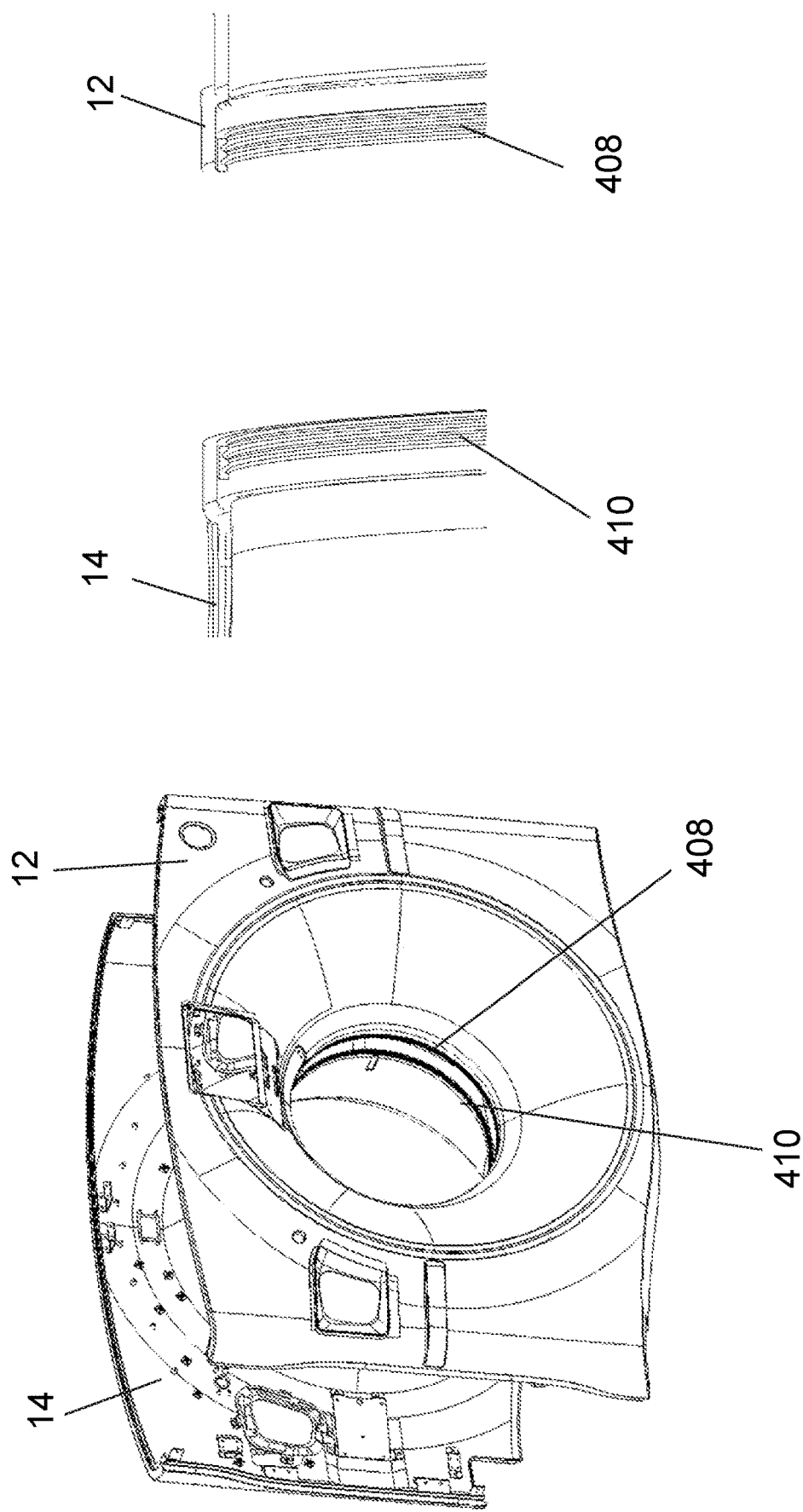
FIG. 4 illustrates a schematic diagram of a first housing 12 and a second housing 14 of the gantry 10 for the CT scanning device according to the first embodiment of the present invention.

FIG. 3 illustrates a schematic diagram of a scan window assembly 30 for the gantry 10 according to a first embodiment of the present invention, exemplarily showing a first window engagement 308 and a second window engagement 310 of the scan window assembly 30. FIG. 4 illustrates a schematic diagram of a first housing 12 and a second housing 14 of the gantry 10 according to a first embodiment of the present invention, exemplarily showing a first housing engagement 408 on the first housing 12 and a second housing engagement 410 on the second housing 14.

Referring to FIG. 3, the scan window assembly 30 may comprise an annular window body 302 (e.g., annular thin layer) having an inner surface and an outer surface, an elastic band 304, an elastic soft sealing material 306, a first window engagement 308 and a second window engagement 310. The scan window assembly 30 may be a detachable component. When the gantry 10 of the scanning device is assembled, the scan window assembly 30 is placed inside the first bore 122 of the first housing 12 and the second bore 142 of the second housing 14 to engage with the first housing 12 and the second housing 14 and cover a gap, i.e., a ray scanning bore, between the first and second bores 122, 142. Such engaging enables a deformation of the annular window body 302 to be limited when an external force is applied on the scan window assembly 30, while the compressed elastic soft sealing material prevents the leakage of liquid inside and outside the scanning device.

The annular window body 302 may be made of a thin layer of material with low X-ray attenuation, have safety protection, and deformability and resilience to restore the original shape when there is no external force. The first window engagement, the second window engagement, the elastic soft sealing material and the elastic band described hereafter are all fixed on the annular window body. In an exemplary embodiment of the present invention, the annular window body 302 may be made of polycarbonate or other thin layer of material with low X-ray attenuation and elasticity.

The elastic band 304 is disposed at both sides of the inner surface of the annular window body 302 along edges of the annular window body 302 to provide elastic pressure to press the scan window assembly 30 towards the first and second housing over an entire circumference inside the first and second bores 122, 142. In exemplary embodiments of the present invention, the elastic band 304 may be composed of stainless steel or other elastic material.

The elastic soft sealing material 306 may be provided on both sides of the outer surface of the annular window body 302 along the edges of the annular window body 302. When the elastic band presses the scan window assembly 30 towards the first and second housing over an entire circumference inside the first and second bores 122, 142, the elastic soft sealing material between the annular window body and a first elastic sealing region on the first housing, and between the annular window body and a second elastic sealing region on the second housing is compressed to achieve a sealed state therebetween, to prevent liquid from leaking between the first housing 12 and the annular window body 302 and between the second housing 14 and the annular window body 302. The elastic soft sealing material 306 may have large deformability and restore the original shape under the action of elastic force when there is no external force. In an exemplary embodiment of the present invention, the elastic soft sealing material 306 may be a relatively soft elastic material, such as foam rubber.

Referring to FIG. 4, the first housing engagement 408 may be fixed inside the bore 122 of the first housing 12 or may be a part of the first housing 12, and the second housing engagement 410 may be fixed inside the bore 142 of the second housing 14 or may be a part of the second housing 14.

The first window engagement 308 and the second window engagement 310 are disposed at both sides of the outer surface of the annular window body 302 respectively. The first window engagement 308 is to engage with the first housing engagement 408 of the first housing 12, and the second window engagement 310 is to engage with the second housing engagement 410 of the second housing 14. The engaging of the first window engagement 308 with the first housing engagement 408 and the engaging of the second window engagement 310 with the second housing engagement 410 are implemented respectively by one of convex/concave surface engaging-lock, Velcro engaging-lock, engaging-lock of rotational contact of convex/concave surface, engaging-lock of surfaces attached closely, and adhesive engaging-lock.

In the present embodiment, the engaging of the first window engagement 308 with the first housing engagement 408 and the engaging of the second window engagement 310 with the second housing engagement 410 are implemented by convex/concave surface engaging-lock. Specifically, the first window engagement 308 and/or the second window engagement 310 comprise one or more tooth arrangements (i.e., convex surface) distributed along a circumferential direction of the annular window body 302. The one or more tooth arrangements have one or more layers of convex teeth in an axial direction of the annular window body 302. The first housing engagement 408 and/or the second housing engagement 410 comprise one or more layers of tooth slots of annular groove (i.e., concave) in the axial direction of the annular window body 302.

Figure 11:
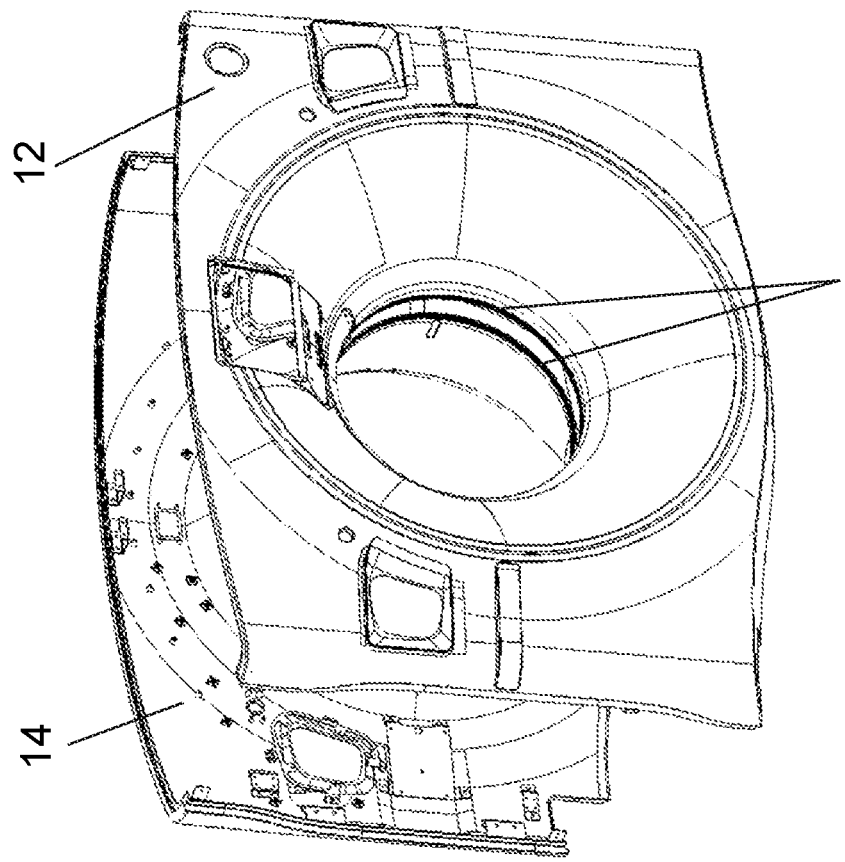
FIG. 11 illustrates 360 degree teeth arrangement distribution in the engaging-lock and sealing structures according to the embodiments of the present invention.
Figure 11:
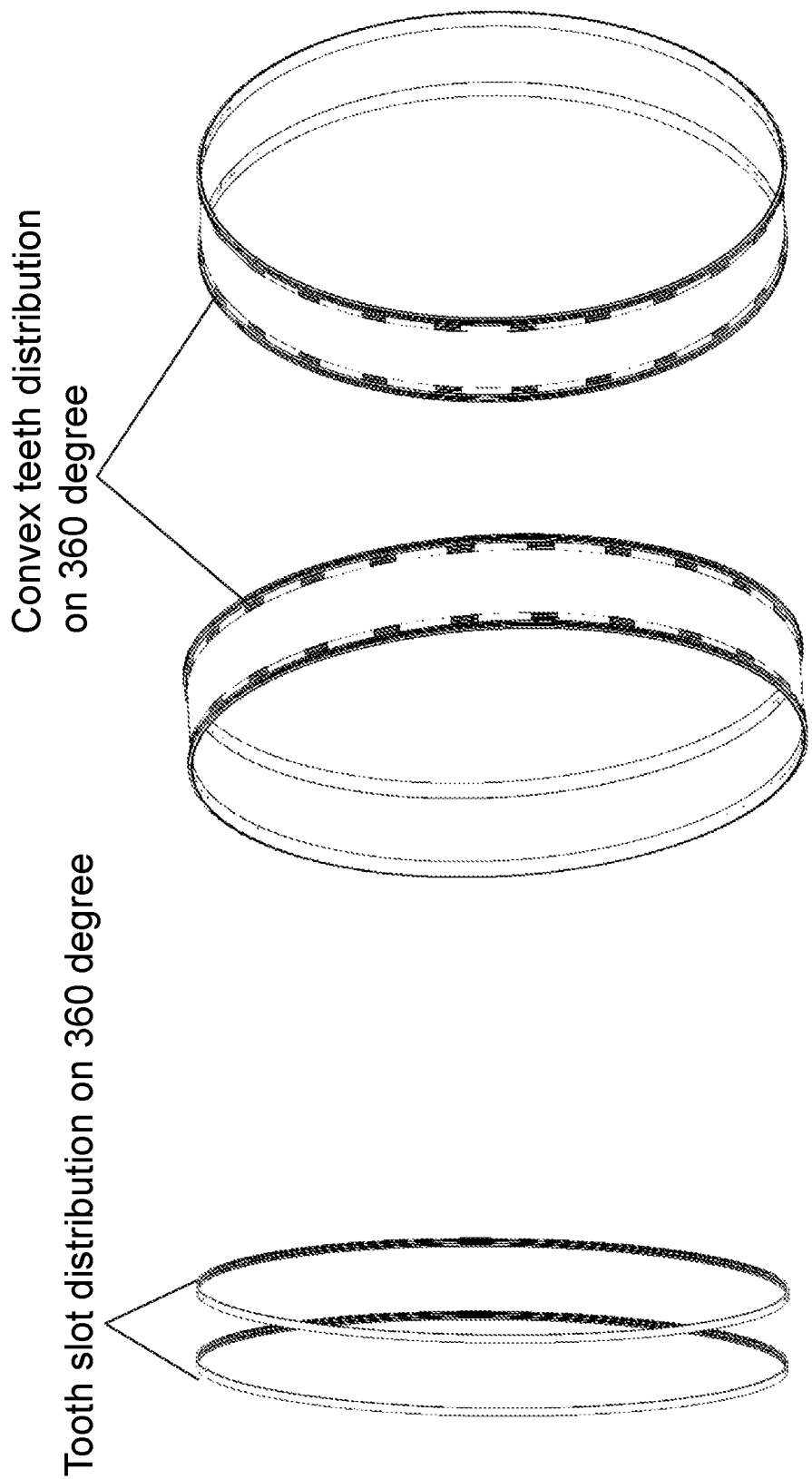
Figure 12:
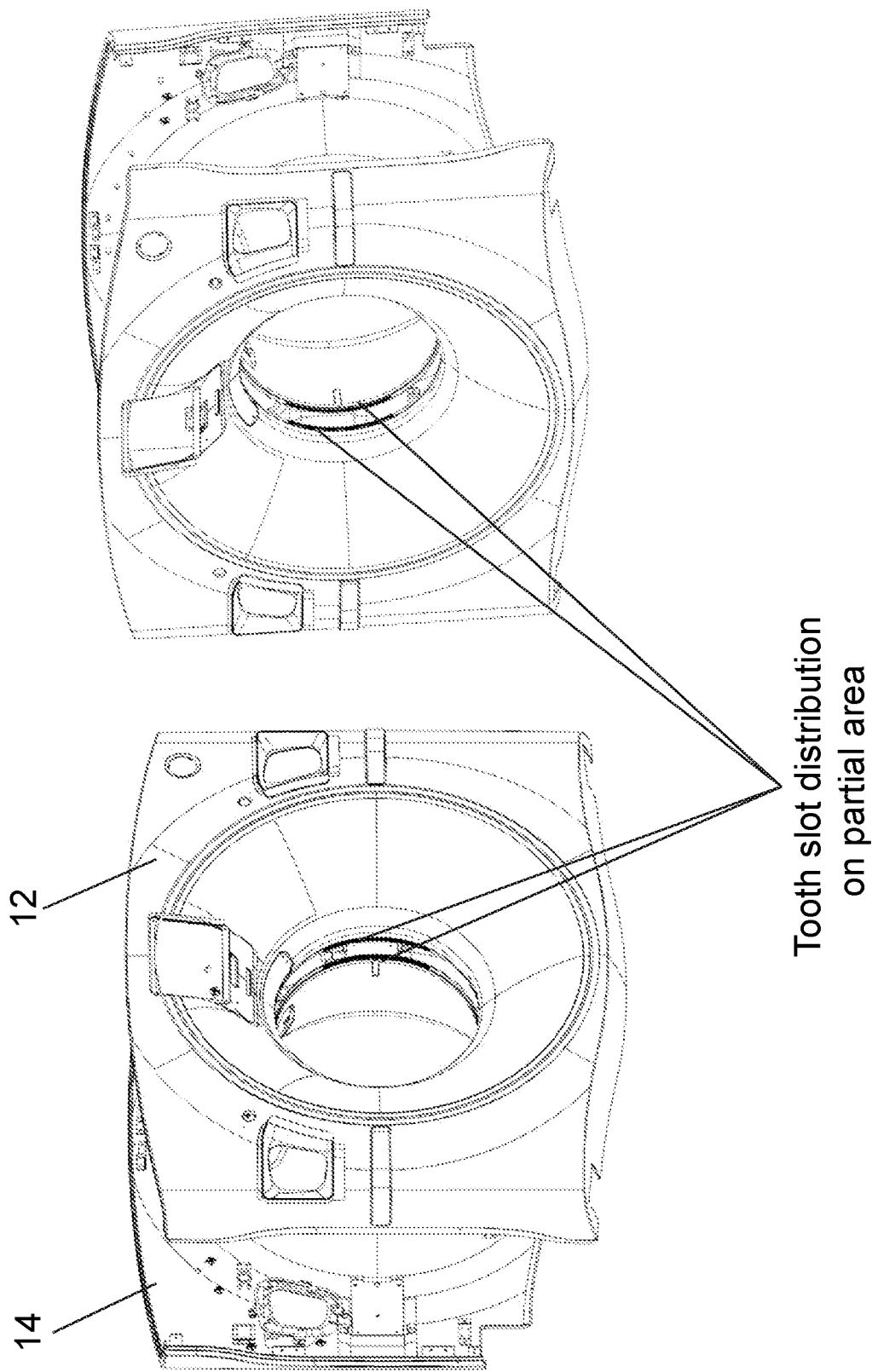
FIG. 12 illustrates partial area teeth arrangement distribution in the engaging-lock and sealing structures according to the embodiments of the present invention.
Figure 12:
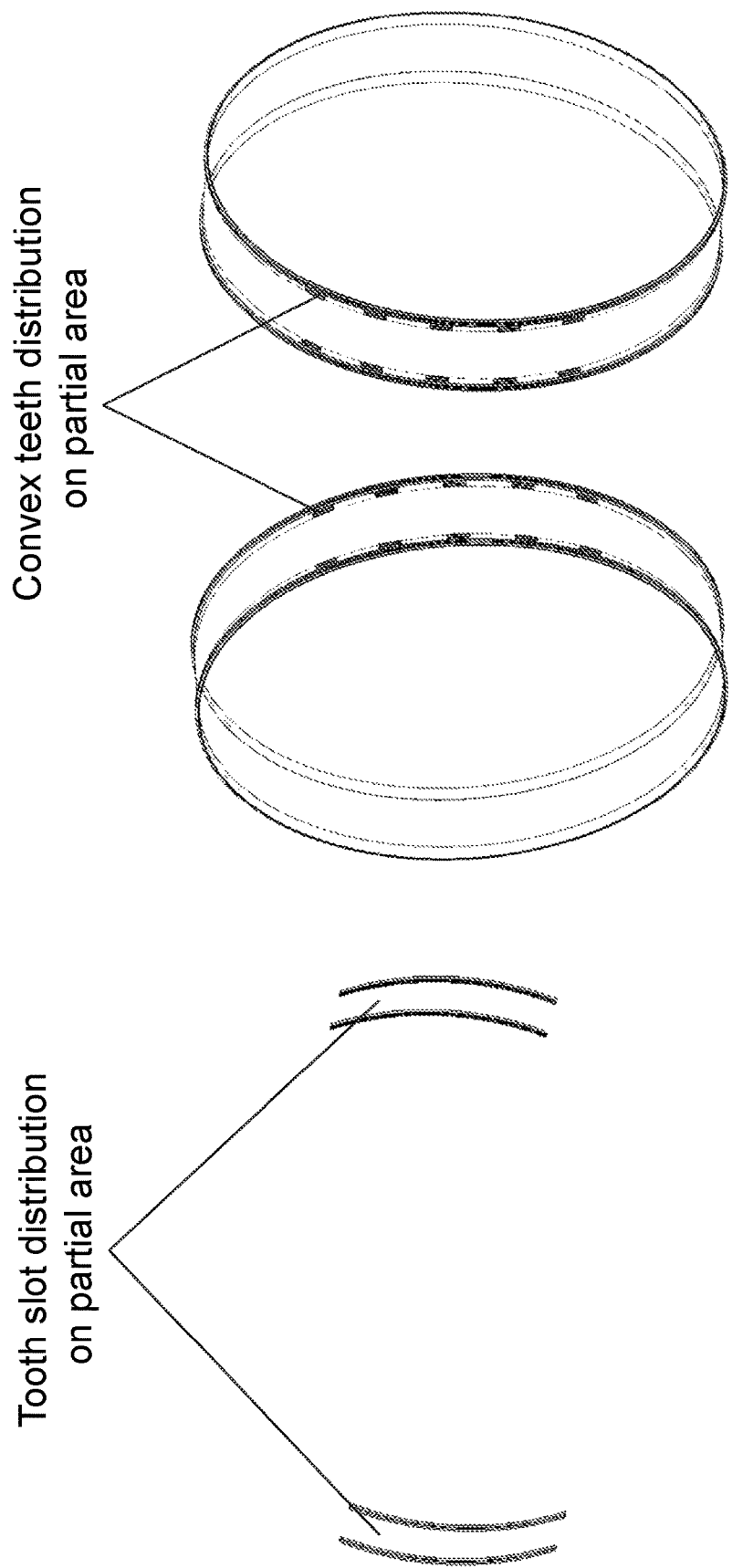

Optionally, as can be seen by combining with FIG. 11, a plurality of tooth arrangements may be distributed around an entire circumference (i.e., 360°) of the annular window body 302, and the tooth slots on the first housing engagement 408 and the second housing engagement 410 are also 360° annular. Alternatively, as shown in FIG. 12, a plurality of tooth arrangements may surround portions of the circumference, instead of the entire circumference, of the annular window body 302, and accordingly, the tooth slots only exist on a partial area of the first housing engagement 408 and the second housing engagement 410.

Figure 13:
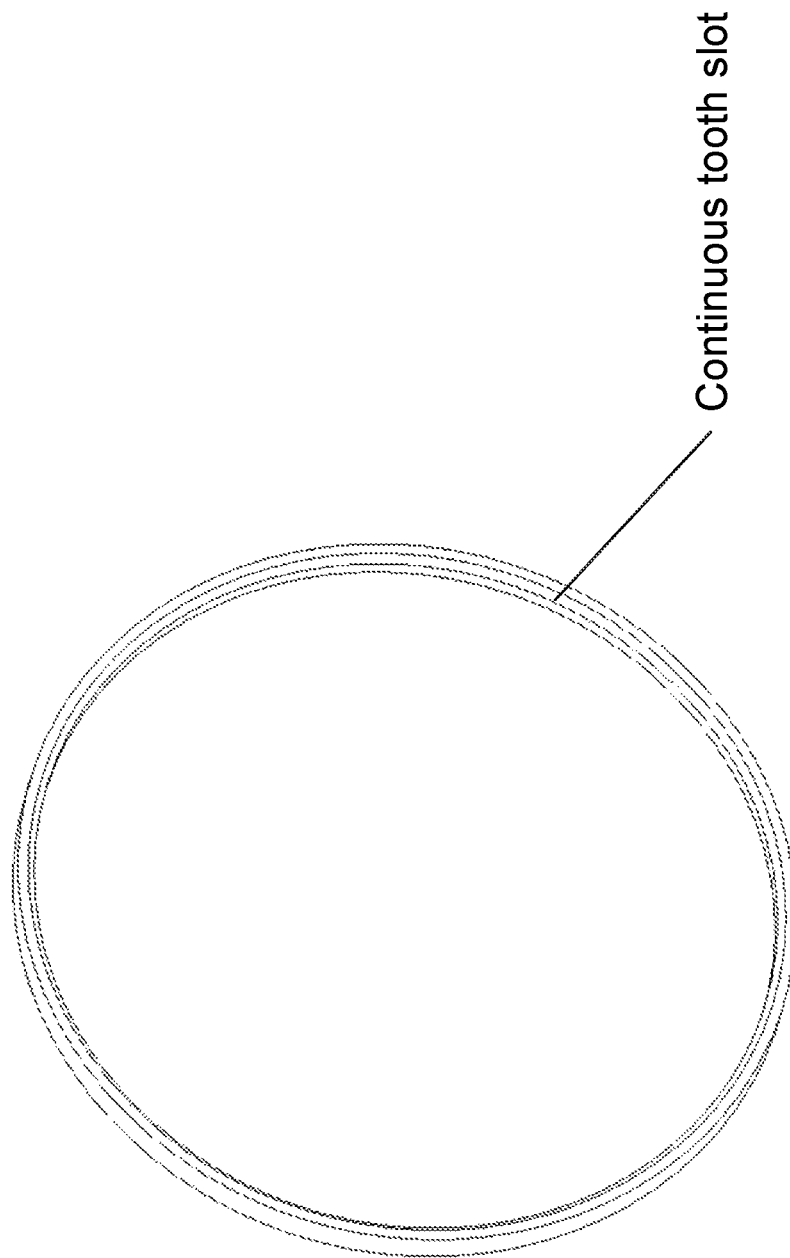
FIG. 13 illustrates continuous teeth slot distribution in the engaging-lock and sealing structures according to the embodiments of the present invention.
Figure 14:
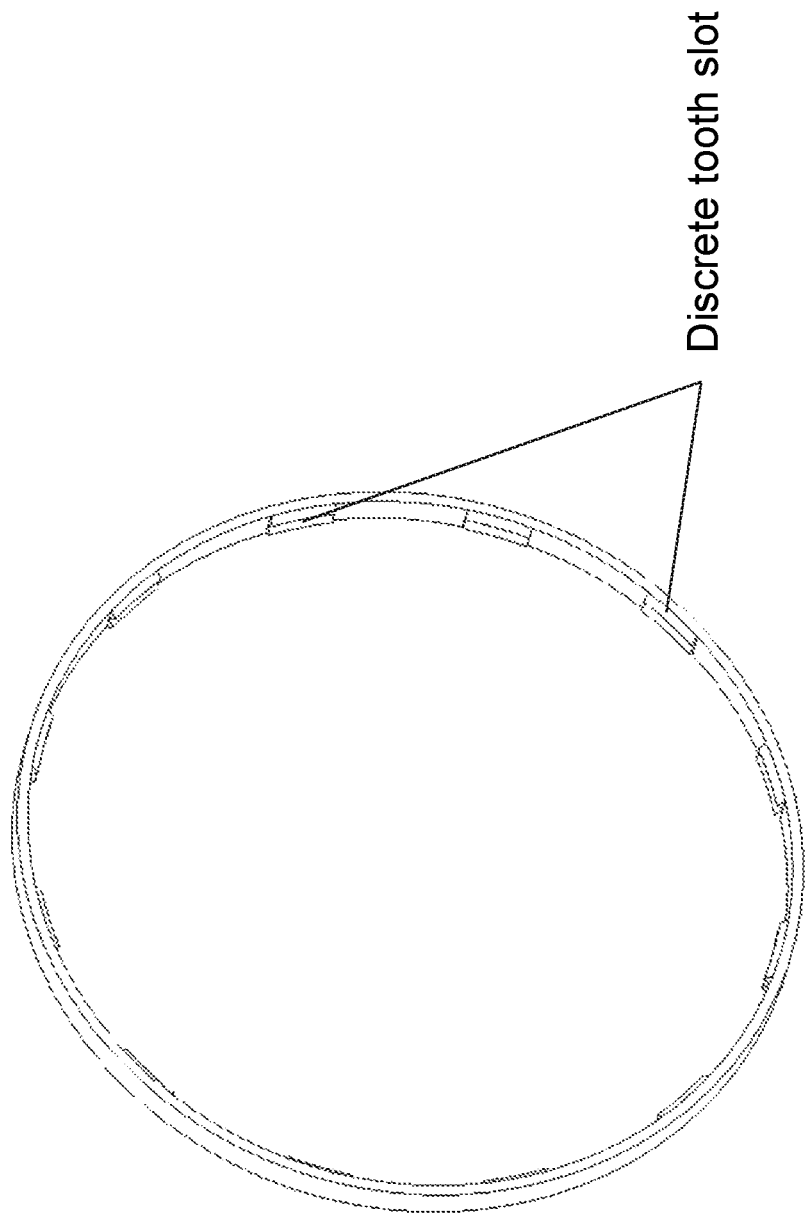
FIG. 14 illustrates discrete teeth slot distribution in the engaging-lock and sealing structures according to the embodiments of the present invention.

In addition, optionally, as shown in FIG. 13, the tooth slots surrounding the circumference of the annular window body 302 may be continuously distributed. Alternatively, as shown in FIG. 14, the tooth slots surrounding the circumference of the annular window body 302 may be discretely distributed at a certain interval.

Moreover, the tooth arrangement may be a convex on a surface of the annular window body 302. For example, the tooth arrangement may be an entity which is formed by a convex section rotating along the outer surface of the annular window body 302, or may be an entity which is formed by a convex section sweeping along the outer surface of the annular window body 302. The tooth slot may be a recess on a surface. For example, the tooth slot may be a concave slot which is formed by a concave section rotating along the inner surface of the bores of the housings, or may be a concave slot which is formed by a concave section sweeping along the inner surface of the bores of the housings. Shape and size of the tooth arrangement are matched with those of the tooth slot. When the tooth arrangement and the tooth slot are engaged, a relative movement and tilt between the tooth arrangement and the tooth slot along an radial direction and an axial direction of the annular window body 302 can be prevented.

In some embodiments, discrete or continuous tooth arrangements may be provided on the scan window assembly 30. When continuous tooth arrangement can ensure that the scan window assembly 30 has sufficient recoverable deformability for its easy assembly and disassembly, the continuous tooth arrangement may be used. When continuous tooth arrangement cannot ensure that the scan window assembly 30 has sufficient recoverable deformability for its easy assembly and disassembly, the discrete tooth arrangements may be used. For example, the scan window assembly 30 may have discrete hard tooth arrangements, or may have continuous semi-hard tooth arrangement. Of course, the scan window assembly 30 may also have discrete semi-hard tooth arrangements, such as discrete rubber tooth arrangements.

Turning back to FIG. 3, in the first embodiment, the first window engagement 308 and the second window engagement 310 are shown as a plurality of tooth arrangements (i.e., convex surfaces) distributed at a certain interval, respectively, and each of the plurality of tooth arrangements has two layers of convex teeth along an axial direction of the annular window body 302. As shown in FIG. 4, the first housing engagement 408 and the second housing engagement 410 each include two tooth slots along the axial direction of the annular window body 302 for being engaging-locked with the corresponding tooth arrangements of two layers of convex teeth on the first window engagement 308 and the second window engagement 310, respectively. Note that, the term " . . . engaging-locked with . . . " herein means that the former and latter engage with each other to interlock.

Figure 5:
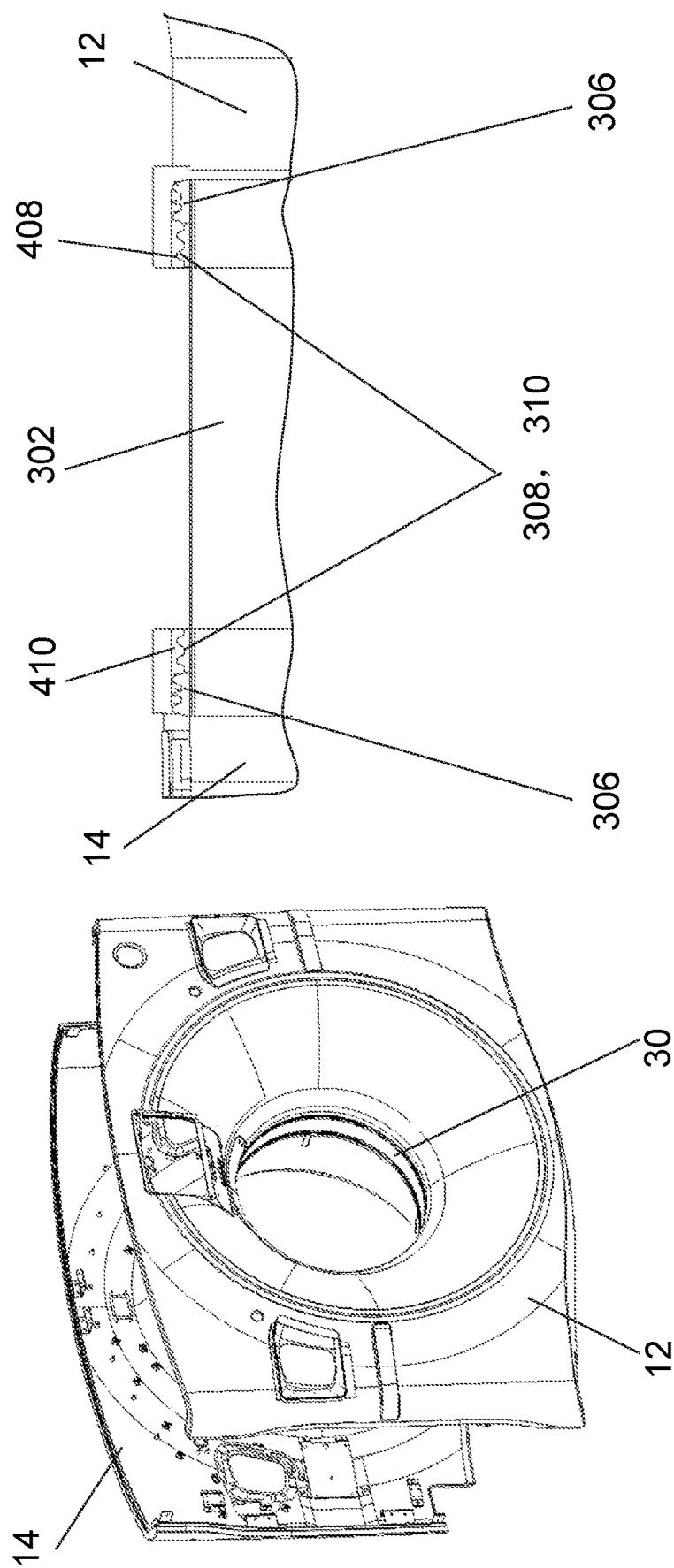
FIG. 5 illustrates a schematic diagram of an engaging-lock and sealing structure between the scan window assembly 30 shown in FIG. 3 and the first and second housings 12, 14 shown in FIG. 4 according to the first embodiment of the present invention.

FIG. 5 illustrates a schematic diagram of an engaging-lock and sealing structure between the scan window assembly 30 shown in FIG. 3 and the first housing 12 and the second housing 14 shown in FIG. 4 according to the first embodiment. The first window engagement 308 and the second window engagement 310 on both sides of the outer surface of the annular window body 302 may be engaged into the first housing engagement 408 and the second housing engagement 410, relatively. The scan window assembly 30 is fixed by engaging-locking each of the window engagements (e.g., tooth arrangements in FIG. 3) with the respective housing engagements (i.e., tooth slots in FIG. 4), thereby achieving the hard or semi-hard engaging between the scan window assembly 30 and the first, second housings 12, 14. Thereby, even if a thinner annular window body (e.g., annular thin layer) is utilized, its deformation would be very low when force is applied thereon. In this way, the scan window assembly 30 can achieve liquid sealing, safety protection for external force, low X-ray attenuation and convenience for easy assembly and disassembly at the same time.

Second Embodiment

Figure 6:
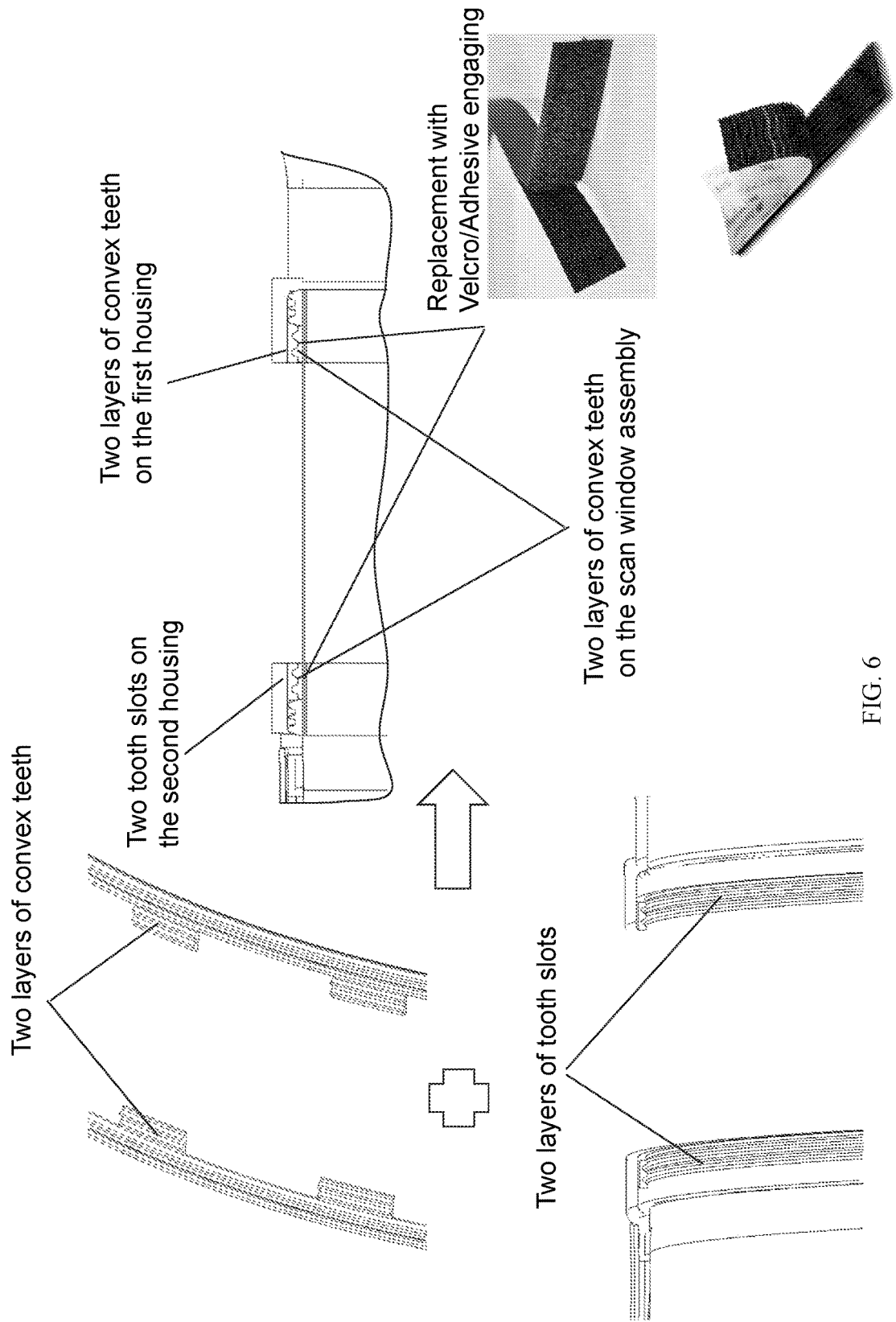
FIG. 6 illustrates a schematic diagram of an engaging-lock and sealing structure between a scan window assembly 30 and a first and second housings 12, 14 according to a second embodiment of the present invention.

FIG. 6 illustrates a schematic diagram of an engaging-lock and sealing structure between a scan window assembly 30 and a first, second housings 12, 14 according to a second embodiment of the present invention. Most of the details of the engaging-lock and sealing structure according to the second embodiment are the same as those of the engaging-lock and sealing structure according to the first embodiment, which will not be repeated in details herein. The differences between the second embodiment and the first embodiment will be mainly described below.

Referring to FIG. 6, instead of the convex/concave surface engaging-lock used in the first embodiment, the engaging-lock and sealing structure according to the second embodiment implements the engaging-lock of the first window engagement 308 with the first housing engagement 408 and the engaging of the second window engagement 310 with the second housing engagement 410 by using Velcro engaging-lock (i.e., HOOK&LOOP).

Specifically, the first window engagement 308 and/or second window engagement 310 as well as the corresponding first housing engagement 408 and/or second housing engagement 410 are Velcro Hook and Velcro Loop, respectively, to constitute a pair of Velcro fastener, thereby achieving the engaging-lock between the scan window assembly 30 and the first, second housings 12, 14.

Third Embodiment

Figure 7:
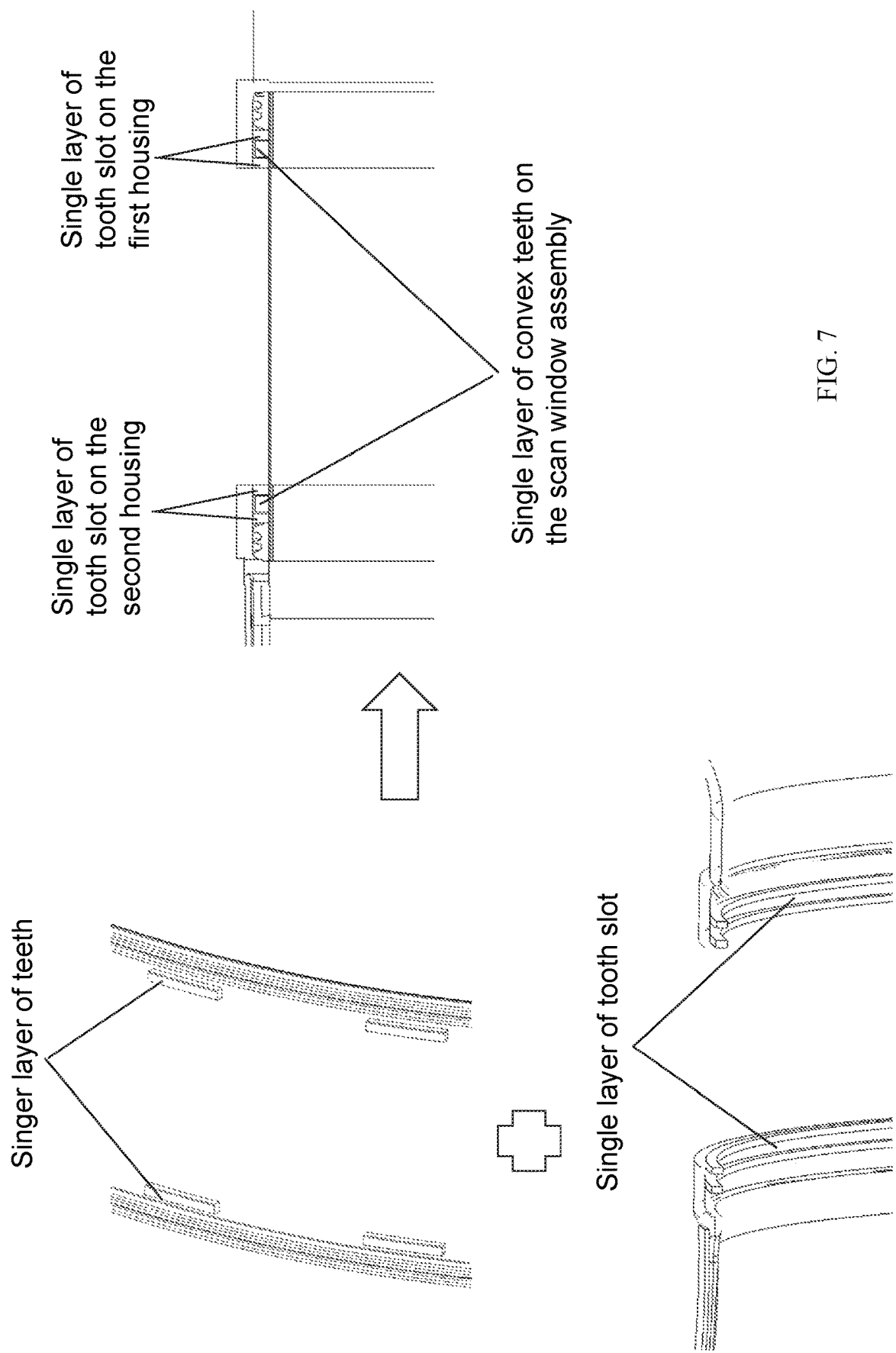
FIG. 7 illustrates a schematic diagram of an engaging-lock and sealing structure between a scan window assembly 30 and a first and second housings 12, 14 according to a third embodiment of the present invention.

FIG. 7 illustrates a schematic diagram of an engaging-lock and sealing structure between a scan window assembly 30 and a first, second housings 12, 14 according to a third embodiment of the present invention. Most of the details of the engaging-lock and sealing structure according to the third embodiment are the same as those of the engaging-lock and sealing structure according to the first embodiment, which will not be repeated in details herein. The differences between the third embodiment and the first embodiment will be mainly described below.

Referring to FIG. 7, instead of the combination of the tooth arrangements of two layers of convex teeth and two layers of tooth slots according to the first embodiment, a plurality of tooth arrangements on the scan window assembly 30 are tooth arrangements of a single layer of convex teeth at both sides of the outer surface of the annular window body 302 in the third embodiment respectively. That is, the first window engagement 308 and/or the second window engagement 310 comprise one or more tooth arrangements (i.e., convex surfaces), the one or more tooth arrangements having a single layer of convex teeth in the axial direction of the annular window body 302, the first and/or second housing engagements 408, 410 comprising one layer of concave tooth slot in the axial direction of the annular window body 302.

Fourth Embodiment

Figure 8:
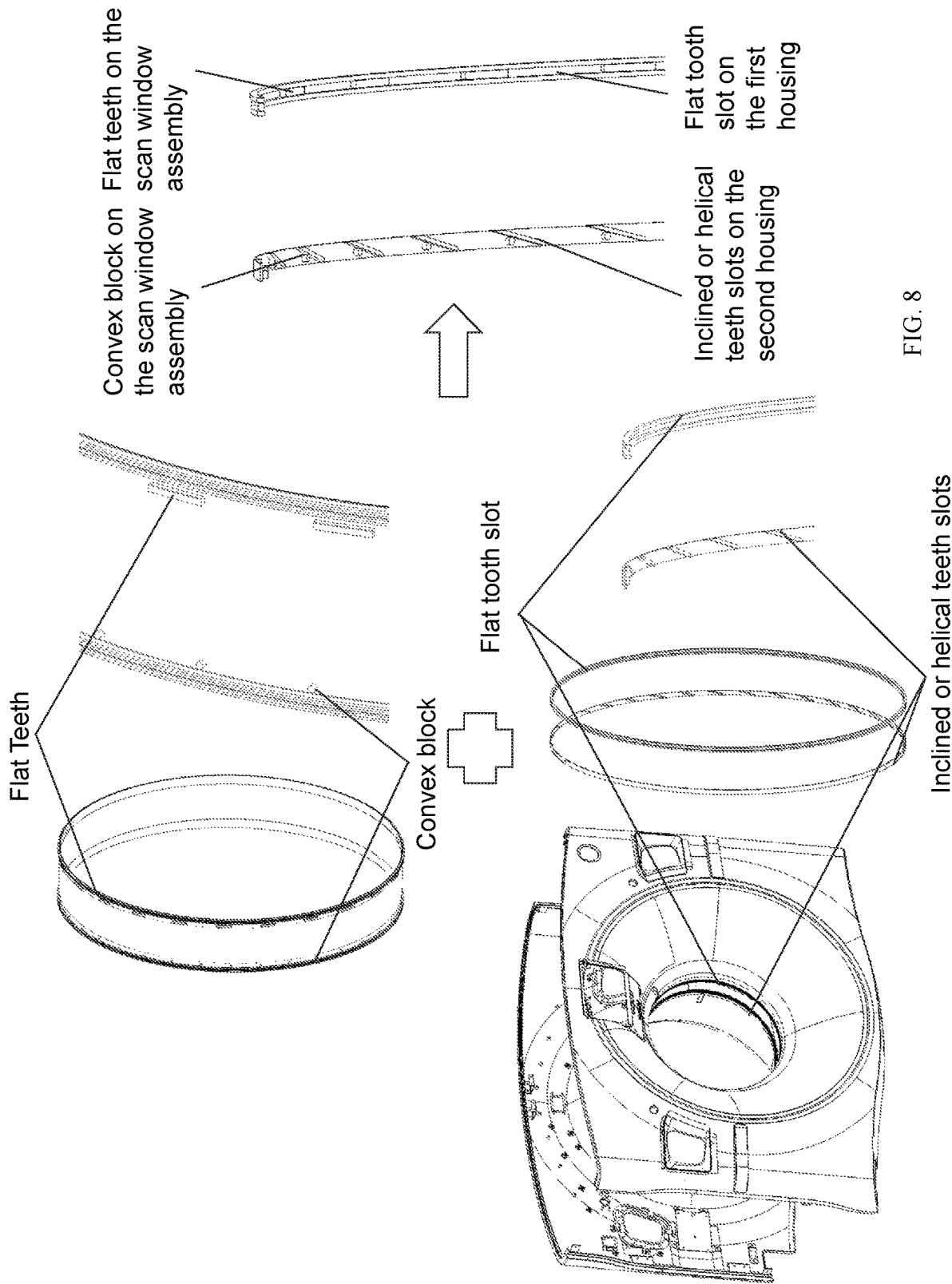
FIG. 8 illustrates a schematic diagram of an engaging-lock and sealing structure between a scan window assembly 30 and a first and second housings 12, 14 according to a fourth embodiment of the present invention.

FIG. 8 illustrates a schematic diagram of an engaging-lock and sealing structure between a scan window assembly 30 and a first, second housings 12, 14 according to a fourth embodiment of the present invention. Most of the details of the engaging-lock and sealing structure according to the fourth embodiment are the same as those of the engaging-lock and sealing structure according to the first embodiment, which will not be repeated in details herein. The differences between the fourth embodiment and the first embodiment will be mainly described below.

Referring to FIG. 8, instead of the combination of the tooth arrangements of two layers of convex teeth and two layers of concave tooth slots according to the first embodiment, the first window engagement 308 comprises one or more flat teeth distributed along the circumferential direction of the annular window body 302 while the second window engagement 310 comprises one or more convex blocks distributed along the circumferential direction of the annular window body 302 in the fourth embodiment. The first housing engagement 408 comprises a flat tooth slot for engaging with the one or more flat teeth, and the second housing engagement 410 comprises one or more inclined or helical inner teeth for engaging with the one or more convex blocks, thereby achieving the engaging-lock between the scan window assembly 30 and the first, second housings 12, 14.

Moreover, the first housing engagement 408 with the flat tooth slots enable the scan window assembly 30 with the flat teeth to freely rotate in the circumferential direction of the annular window body 302 without a movement in the axial direction, so that the scan window assembly 30 can rotate, until the convex blocks on the scan window assembly 30 contact the surface of the inclined or helical inner teeth of the second housing engagement.

Fifth Embodiment

Figure 9:
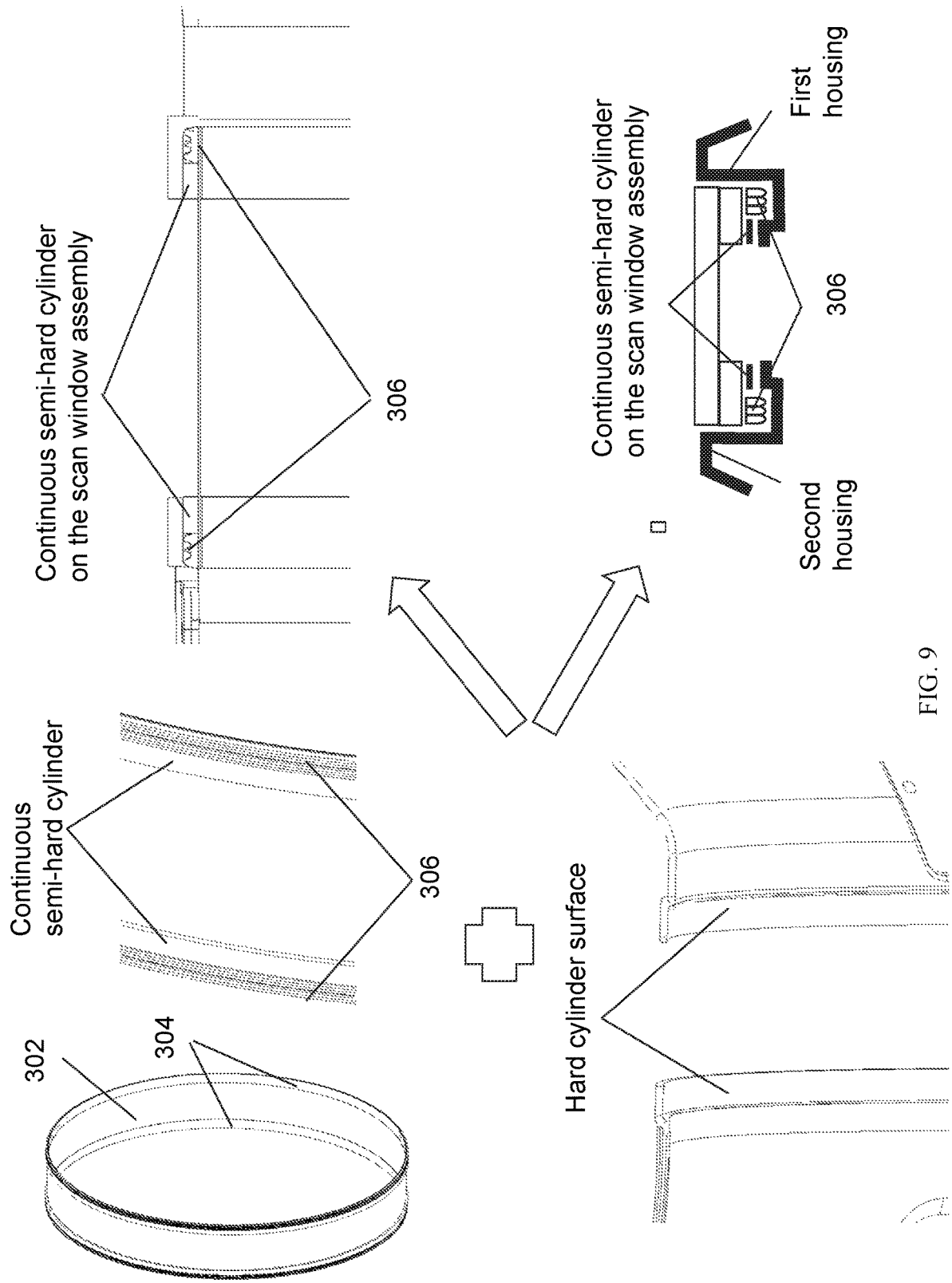
FIG. 9 illustrates a schematic diagram of an engaging-lock and sealing structure between a scan window assembly 30 and a first and second housings 12, 14 according to a fifth embodiment of the present invention.
Figure 10:
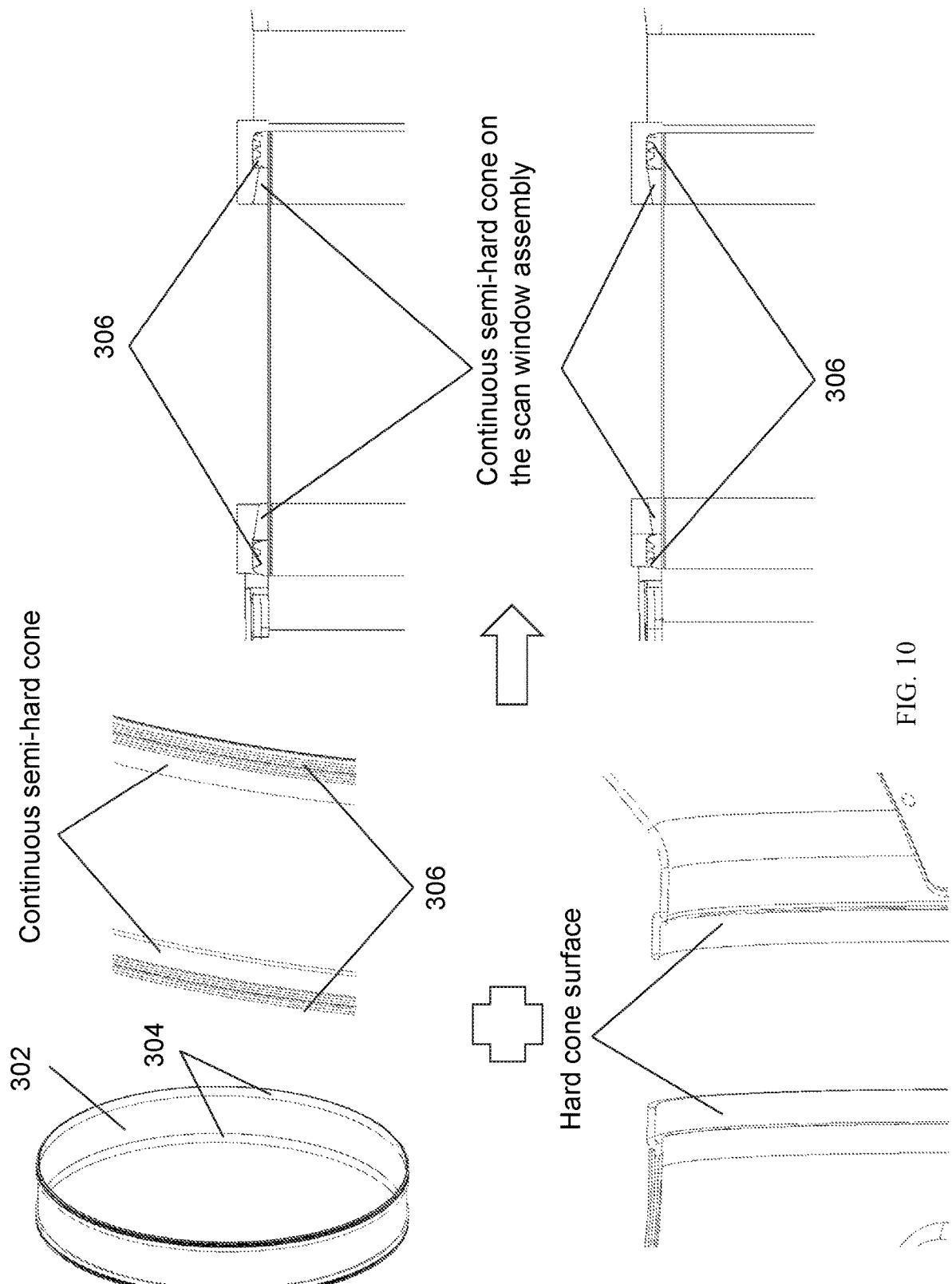

FIGS. 9&10 illustrate a schematic diagram of an engaging-lock and sealing structure between a scan window assembly 30 and a first, second housings 12, 14 according to a fifth embodiment of the present invention. Most of the details of the engaging-lock and sealing structure according to the fifth embodiment are the same as those of the engaging-lock and sealing structure according to the first embodiment, which will not be repeated in details herein. The differences between the fifth embodiment and the first embodiment will be mainly described below.

Instead of the convex/concave surface engaging-lock used in the first embodiment, the fifth embodiment implements the engaging-lock of the first window engagement 308 with the first housing engagement 408 and the engaging of the second window engagement 310 with the second housing engagement 410 by using the engaging-lock of surfaces attached closely. In case of implementing by the engaging-lock of surface attached closely, the first and/or second window engagement has a continuous cylinder shape or continuous cone shape and consists of semi-hard material, and the first and/or second housing engagement has a cylinder or cone hard internal surface to match the cylinder-shaped or cone-shaped first and/or second window engagement. The semi-hard material may refer to a material having certain deformability and a resilience to restore the original shape when there is no external force, to ensure that the scan window assembly 30 has sufficient recoverable deformability to facilitate its assembly and disassembly.

Theoretically, the engaging of surface attached closely may be considered as a particular case of the convex/concave engaging when the convexity/concavity of the convex/concave surface is approaching to zero, in which the engaging becomes a cylinder or cone engaging. When force is applied on the scan window assembly 30, the semi-hard cylinder or cone engaging can limit deformation of the annular window body 302.

Specifically referring to FIG. 9, the first window engagement 308 and the second window engagement 310 are continuous semi-hard cylinders, and the first housing engagement 408 and the second housing engagement 410 have cylinder hard internal surfaces for respectively engaging with the first window engagement 308 and the second window engagement 310 which are continuous semi-hard cylinders, thereby achieving the semi-hard engaging-lock between the scan window assembly 30 and the first, second housings 12, 14.

Further referring to FIG. 10, the first window engagement 308 and the second window engagement 310 are continuous semi-hard cones, and the first housing engagement 408 and the second housing engagement 410 have cone hard internal surfaces for respectively engaging with the first window engagement 308 and the second window engagement 310 which are continuous semi-hard cones, thereby achieving the semi-hard engaging between the scan window assembly 30 and the first, second housings 12, 14.

In either of both cases (cylinder engaging-lock or cone engaging-lock) as mentioned above, the first window engagement 308 and second window engagement 310 in cylinder or cone shape on the scan window assembly 30 are formed of materials with a suitable stiffness (i.e., semi-hard). Meanwhile, a sufficiently high coefficient of friction and force of friction are required between the materials of the cylindrical or conical first window engagement 308 and the first housing engagement 408 and between the materials of the second window engagement 310 and the second housing engagement 410 on the scan window assembly 30 to prevent relative sliding therebetween. Specifically, for example, a rubber material may be used as one of the materials having a suitable hardness for the cylindrical or conical first window engagement 308 and the second window engagement 310. Due to the high coefficient of friction between the engaging lockers, there is a large force of friction under the elastic pressure of the elastic band 304, which can prevent relative movement between the scan window assembly 30 and the first, second housings 12, 14 of the gantry. Of course, any other material with suitable hardness and coefficient of friction may also be used, as long as it can prevent relative movement between the scan window assembly 30 and the first, second housings 12, 14 of the gantry.

For example, the first window engagement 308 and/or the second window engagement 310 of the scan window assembly 30 may be composed of a cylinder-shaped or cone-shaped semi-hard material discretely distributed along the annular scan window body 302.

Six Embodiment

FIG. 6 illustrates a schematic diagram of an engaging-lock and sealing structure between a scan window assembly 30 and a first, second housings 12, 14 according to a sixth embodiment of the present invention. Most of the details of the engaging-lock and sealing structure according to the sixth embodiment are the same as those of the engaging-lock and sealing structure according to the first embodiment, which will not be repeated in details herein. The differences between the sixth embodiment and the first embodiment will be mainly described below.

Referring to FIG. 6, instead of the convex/concave surface engaging-lock used in the first embodiment, the engaging-lock and sealing structure according to the sixth embodiment implements the engaging-lock of the first window engagement 308 with the first housing engagement 408 and the engaging of the second window engagement 310 with the second housing engagement 410 by using engaging-lock of an adhesive that can be disassembled multiple times.

The above engaging-lock and sealing structures according to the second to sixth embodiments may be used in combination with each other, or may be partially or entirely used in combination with the first embodiment. Like the first embodiment, the engaging-lock and sealing structures according to those embodiments make it possible to have a low deformation when force is applied, even though a thinner annular window body (e.g., annular thin layer) is used. In this way, the scan window assembly 30 can achieve liquid sealing, safety protection for external force, low X-ray attenuation and convenience for easy assembly and disassembly at the same time. However, it should be noted that the engaging-lock and sealing structures in accordance with the present invention are not only limited to the specific embodiments described herein, but also may include other alternative implementations. For example, other types of engaging-locking tooth arrangements can be used, or the annular window body itself can have the functionality of tooth arrangement to directly adhere to the first housing and the second housing to engage and lock, and other numbers of tooth layers can also be used. As another example, other distributions of tooth arrangements may be provided, or different types of engagements may be combined at both sides of the outer surface of the scan window assembly.

The scan window assembly for a CT scanning device and the CT scanning device comprising the same according to the exemplary embodiments of the present invention have been described in details above. The scan window assembly comprises the combination of the hard or semi-hard engaging, the elastic soft material sealing and the pressing of the elastic band. Particularly, the elastic soft sealing material seals liquid leakage in/out between the enclosure of the scanning device and the scan window to get high-waterproof; the hard or semi-hard engaging can limit the tilting and movement of the elastic band and the scan window assembly to reduce the deformation of the scan window; the elastic band can provide pressure to press the scan window toward an radially outward direction of the bores of the enclosure of the gantry to keep the sealing and engaging thereof; the elasticity of the annular window body also can provide a similar pressure. The above configuration also enables the scan window assembly to have certain elastic deformability for easy assembly and disassembly.

Moreover, the CT scanning device comprising the above scan window assembly particularly has the following advantages:

1) Keeping Safety Protection Against External Force for Thinner Scan Window

Because of the engaging-lock and sealing structure is used between the scan window assembly and the enclosure of the scanning device, deformation of the annular window body is reduced, which means that, for example, the patient body will be safe even if special elbows of the patient's body press hard on the thinner window body.

2) Getting Lower X-Ray Attenuation for Lower Deformation of the Annular Window body Due to the lower deformation of the annular window body, a thinner scan window layer may be used under patient force safety condition, which brings lower X-ray attenuation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled.

The invention claimed is:

1. A gantry of a CT scanning device, comprising:
a first housing having a first bore;
a second housing having a second bore, the second housing positioned opposite to the first housing, and the first housing coupled to the second housing; and
a scan window assembly positioned in a gap between the first bore of the first housing and the second bore of the second housing, the scan window assembly comprising:
an annular window body having an inner surface facing an opening of the first bore and the second bore and an outer surface opposite the inner surface facing away from the opening;
a first band positioned around a first inner surface edge of the annular window body;
a second band positioned around a second inner surface edge of the annular window body;
a first soft sealing member positioned around a first outer surface edge of the annular window body;
a second soft sealing member positioned around a second outer surface edge of the annular window body;
a first plurality of fastening members positioned adjacent to the first soft sealing member on the annular window body;
a second plurality of fastening members positioned adjacent to the second soft sealing member on the annular window body;
a first window engagement member positioned around an outer surface edge of the first housing for engaging the annular window body with the first housing; and
a second window engagement member positioned around an outer surface edge of the second housing for engaging the annular window body with the second housing.

2. The gantry according to claim 1, wherein the engaging of the first window engagement member with the first housing and the engaging of the second window engagement member with the second housing are implemented respectively by one of a convex/concave surface engaging-lock, an engaging-lock of rotational contact of convex/concave surface, an engaging-lock of surfaces attached closely, an adhesive engaging-lock; and a hook and loop engaging-lock.

3. The gantry according to claim 2, wherein the engaging of the first window engagement member with the first housing and the engaging of the second window engagement member with the second housing is implemented by the convex/concave surface engaging-lock, the first and/or second window engagement comprises a tooth arrangement, the tooth arrangement having one or more layers of convex teeth in an axial direction of the annular window body, the first and/or second housing comprising one or more layers of concave tooth slots in the axial direction of the annular window body.

4. The gantry according to claim 2, wherein the engaging of the first window engagement member with the first housing and the engaging of the second window engagement member with the second housing is implemented by the engaging-lock of rotational contact of convex/concave surface, the first window engagement member comprises one or more teeth distributed along a circumferential direction of the annular window body, the second window engagement member comprises one or more convex blocks distributed along the circumferential direction of the annular window body, the first housing comprising tooth slots for engaging with the one or more teeth, the second housing comprising one or more inclined or helical tooth slots for engaging with the one or more convex blocks.

5. The gantry according to claim 2, the engaging of the first window engagement member with the first housing and the engaging of the second window engagement member with the second housing is implemented by the engaging-lock of surface attached closely, the first and/or second window engagement member has a cylinder shape or cone shape and consists of semi-hard material, the first and/or second housing has a cylinder or cone hard internal surface corresponding thereto.

6. The gantry according to claim 2, wherein the engaging of the first window engagement member with the first housing and the engaging of the second window engagement member with the second housing is implemented by adhesive engaging-lock, the engaging-lock of the first and/or second window engagement member and the corresponding first and/or second housing engagement is formed by using an adhesive that can be disassembled multiple times.

7. The gantry according to claim 1, wherein the first and/or second window engagement member is continuous along a circumferential direction of the annular window body.

8. The gantry according to claim 1, wherein the first and/or second window engagement member has a plurality of sub-engagements along a circumferential direction of the annular window body.

9. The gantry according to claim 1, wherein the first and/or second window engagement member surrounds an entire circumference of the annular window body, or the first and/or second window engagement member surrounds a partial circumference of the annular window body.

10. The gantry according to claim 1, wherein the first band and the second band are elastic bands that provide pressure to press the scan window assembly towards the first housing and the second housing along its radially outward direction over an entire circumference.

11. The gantry according to claim 1, wherein the first soft sealing member and the second soft sealing member are made of an elastic soft sealing material, the elastic soft sealing material being compressible and deformable under an elastic pressure of the scan window assembly to achieve the sealing of the first housing and the scan window assembly, and the sealing of the second housing and the scan window assembly.

* * * * *